United States Patent [19]

Hobbs et al.

[11] Patent Number: 5,346,470
[45] Date of Patent: Sep. 13, 1994

[54] CONTRAST MEDIA INJECTOR

[75] Inventors: Eamonn Hobbs, Queensbury, N.Y.;
Irvin F. Hawkins, Mincanopy, Fla.;
Arthur Zimmet, Centerport, N.Y.;
John Goodman, Huntington, N.Y.;
Daniel Recinella, Hadley, N.Y.

[73] Assignee: E-Z-EM, Inc., Westbury, N.Y.

[21] Appl. No.: 9,861

[22] Filed: Jan. 27, 1993

Related U.S. Application Data

[60] Continuation-in-part of Ser. No. 931,908, Aug. 17, 1992, which is a division of Ser. No. 629,180, Dec. 20, 1990, Pat. No. 5,249,579.

[51] Int. Cl.$^5$ ............................................. A61M 37/00
[52] U.S. Cl. ......................................... 604/24; 604/26; 604/30
[58] Field of Search .................... 604/23, 24, 26, 30, 604/32, 34; 128/635, 655

[56] References Cited

U.S. PATENT DOCUMENTS

| | | | |
|---|---|---|---|
| 3,375,823 | 4/1968 | Pamplin et al. | 604/26 |
| 3,631,847 | 1/1972 | Hobbs | 604/49 |
| 3,769,962 | 11/1973 | McVey | 604/24 |
| 3,812,843 | 5/1974 | Wooten et al. | 128/655 |
| 3,870,072 | 3/1975 | Lindemann | 128/3 |
| 3,880,138 | 4/1975 | Wooten et al. | 128/655 |
| 4,137,913 | 2/1979 | Georgi | 604/67 |
| 4,392,847 | 7/1983 | Whitney et al. | 128/655 |
| 4,464,169 | 8/1984 | Semm | 604/26 |
| 4,878,894 | 11/1989 | Sutter, Jr. et al. | 604/24 |
| 4,895,144 | 1/1990 | Cook et al. | 604/30 |

*Primary Examiner*—C. Fred Rosenbaum
*Assistant Examiner*—Michael Rafa
*Attorney, Agent, or Firm*—McAulay Fisher Nissen Goldberg & Kiel

[57] ABSTRACT

An apparatus is provided for use with a contrast media injector. The injector is of the type including a gas source and a liquid source. The apparatus includes a gas delivery channel connected to the gas source and a liquid delivery channel connected to the liquid source. Two normally closed valves are provided to control flow from the gas and liquid channel. The valves insure that gas and liquid do not simultaneously exit from the channel. The valves minimize inadvertent mixing of the gas and saline downstream of the valves. The gas channel is connected to a gas source using a fitting which also connects electro-conductive wires in the apparatus to a power source. The liquid channel connects to a source of liquid.

9 Claims, 6 Drawing Sheets

CONTRAST MEDIA INJECTOR

This is a Continuation-In-Part of U.S. patent Application No. 931,908 filed on Aug. 17, 1992 pending, which is in turn, a division of U.S. patent Application Ser. No. 629,180, filed on Dec. 20. 1990 now U.S. Pat. No. 5,249,579.

BACKGROUND OF THE INVENTION

The present invention relates to an injector for injecting a gas contrast media into the bloodstream and more particularly to such an injector for injecting carbon dioxide into the bloodstream in a controlled manner.

Carbon dioxide injected into the blood stream can serve as a negative contrast media for angiographic procedures or as a blood displacement media for procedures such as arteriograms, angioscopy and laser therapy.

Liquid iodinated contrast is one presently used contrast media for angiography. The liquid iodinated contrast is injected into the bloodstream at a predetermined flow rate. When liquid iodinated contrast enters the bloodstream, it mixes with the blood and flows downstream. Although iodinated contrast media is generally useful and safe, it can create serious problems and even death in people with iodine allergies.

Saline is a known blood displacement media and is frequently used during laser therapy and angioscopy. Saline has limited use as it cannot be safely injected in large doses. Carbon dioxide, in contrast to saline, has superior light transmittance and thermal insulating properties.

Carbon dioxide, in contrast to known prior art contrast and displacement media, is inexpensive, non-toxic, and is readily released from the body by the normal breathing process. However, there have been problems safely and effectively using carbon dioxide as a contrast media with presently known delivery systems due, in part, to the fact that carbon dioxide is a compressible gas.

When carbon dioxide is injected into the vascular system, it compresses and expands along with the pressure wave created by the cardiac output. Blood forced into the aorta during cardiac systole moves the blood forward in the blood vessels and sets up a pressure wave which travels down the arteries. The arterial pressure rises during systole and lowers during diastole.

The flow rate of blood through the vascular system depends upon the cardiac cycle and blood pressure. The flow rate can be measured directly using known means.

When carbon dioxide is injected into the bloodstream, it forms bubbles. Carbon dioxide does not mix with the blood. For carbon dioxide to function as a viable contrast media or displacement media, it must completely displace the blood in the area of interest. If it does not, any area of blood not displaced will falsely appear to be a stenosis or lesion. The carbon dioxide must completely displace the blood in the area of interest for the entire injection period. For this displacement to occur the carbon dioxide must be injected at a pressure greater than the pressure of the blood itself. However, if the pressure differential between the injected carbon dioxide and the blood is too great a reflux or retrograde flow of carbon dioxide occurs. This reflux necessitates the injection of additional carbon dioxide and further creates safety problems due to the uncontrolled nature of the carbon dioxide flow.

Care must be taken with carbon dioxide to prevent blood clots from forming. Additionally, care must be taken to prevent any pressure spike at the initiation of the carbon dioxide injection. Additionally, care must be taken to avoid an explosive delivery which can cause patient pain. In order to avoid an explosive delivery care must be taken to establish a continuous column of carbon dioxide before an injection is commenced. Further, nitrogen and oxygen should be removed from the injector system to insure patient safety and comfort.

During the angiographic procedure it is advisable to flush the catheter, through which the carbon dioxide is introduced, with saline. Saline is injected whenever the flow of carbon dioxide is halted to avoid clotting of blood. It is important that all of the saline is evacuated from the system before carbon dioxide is injected and vice versa. If carbon dioxide is in the system while blood pressure is taken, the blood pressure wave may be dampened. If saline is in the system when carbon dioxide is injected, erratic delivery of the carbon dioxide may occur.

It is preferable to inject as little carbon dioxide as possible without sacrificing the integrity of the procedure and, it is preferable to have the carbon dioxide injected at the lowest pressure which still permits complete displacement of blood.

Accordingly, it is an object of the present invention to provide a device for introducing carbon dioxide into the bloodstream such that carbon dioxide can function as a contrast and blood displacement medium.

It is another object of the present invention to provide such a device which enables the carbon dioxide to completely displace the blood in the area of interest for the entire injection.

It is yet another object of the present invention to provide such a device which minimizes safety hazards and enhances patient comfort.

Yet a further object of the present invention is to provide such a device which minimizes problems, such as blood clots or explosive delivery.

Still a further object of the invention is to provide a mechanism for safely and efficiently delivering a saline drip in conjunction with the delivery of the carbon dioxide.

It is another object of the invention to provide an economical electro-gas connector that helps prolong the useful life of the receptacle on the injector.

BRIEF DESCRIPTION

In one embodiment of the present invention an apparatus for use with a contrast media injector is provided. The injector is of the type including a source of gas and a source of liquid. The apparatus includes a gas delivery channel, and a liquid delivery channel. Means is provided to connect the gas channel to a gas source and means is provided to connect the liquid delivery channel to a liquid source. Valve means for controlling the flow of gas and liquid from the gas and liquid channels is provided. The valve means insures that the gas and liquid do not simultaneously exit from their respective channels. The valve means further insures the minimizing of mixing of the gas and liquid. The means for connecting the gas channel to the gas source includes means to connect electro-conductive wires to a power source.

DETAILED DESCRIPTION OF THE PREFERRED EMBODIMENT

Figure 1:
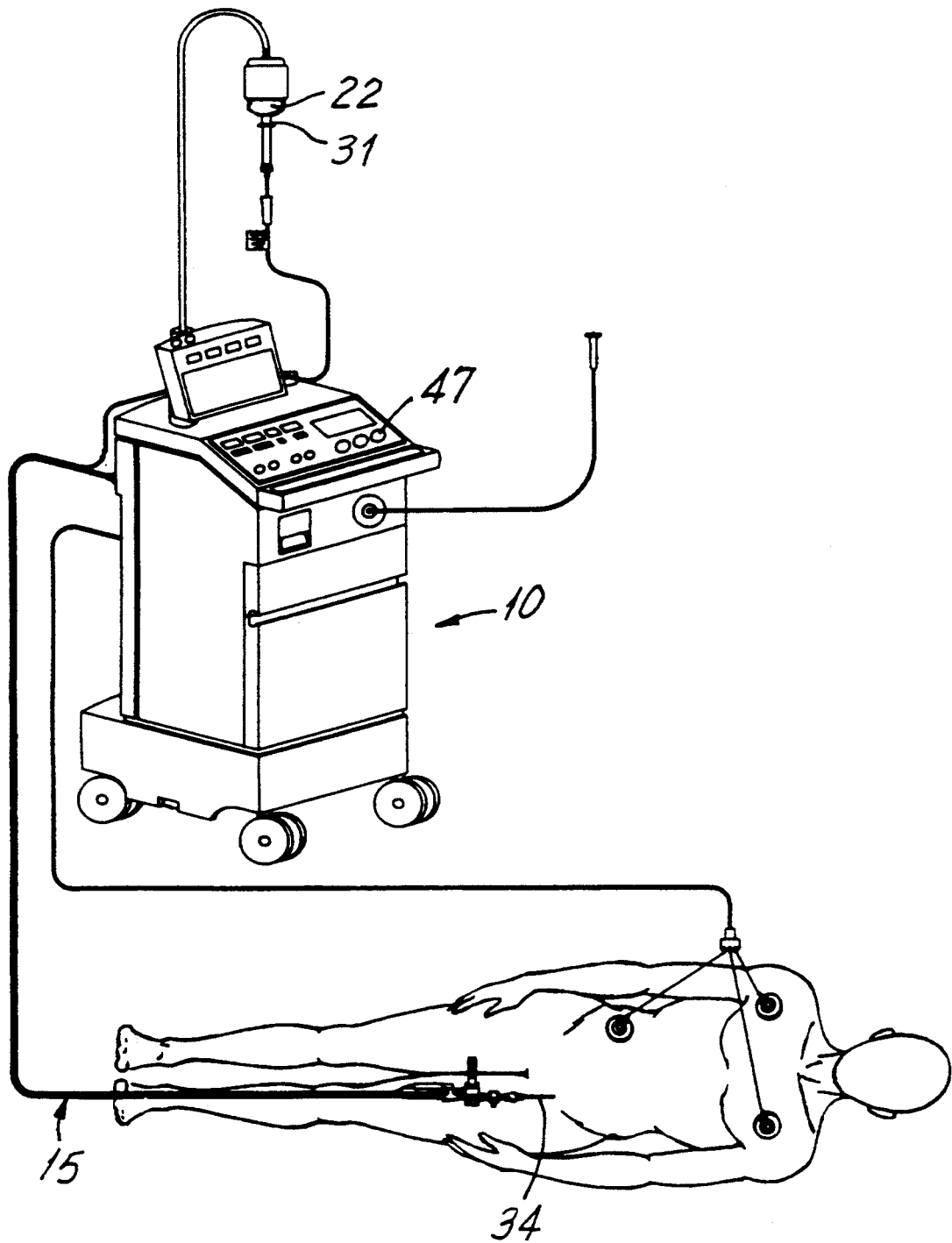
FIG. 1 is a schematic view of the apparatus of the present invention connected to both a contrast media injector and a patient.

Referring now to the drawings, the reference numeral 10 generally denotes the contrast media injector of the present invention. Injector 10 is capable of delivering carbon dioxide, or any other appropriate gas, to a person's bloodstream in a controlled, variable manner which synchronizes the flow of the injected carbon dioxide to the pulsatile flow of the blood in the area to be studied.

Injector 10 uses carbon dioxide from a carbon dioxide source (not shown). In a preferred embodiment of the invention, a disposable TA4 cylinder which contains a predetermined volume of carbon dioxide is used as the source of carbon dioxide.

Carbon dioxide flows from the cylinder through the injector 10, through a sterile tube set 15 and is then introduced into a patient's blood stream via a catheter 34. The flow rate of the carbon dioxide is controlled by a valve 20, in injector 10, which has a variable orifice. Valve 20 is in turn controlled by a microprocessor 12. In a preferred embodiment of the invention, valve 20 is a DC controlled valve which is capable of regulating gas flow rates between 3 cc/sec to 225 cc/sec. In use the valve is regulated to a first higher flow rate during systole and a second lower flow rate during diastole. The response time of the valve orifice in switching between the systolic and diastolic flow rates is about 3 milliseconds.

Other means to control flow may be used instead of a variable orifice valve. Examples of such means is the use of a two intermediate reservoir system which holds the carbon dioxide at two different pressures, a series of cascading valves coupled to calibrated orifices, and two variable pressure regulators.

The orifice of valve 20 is controlled by a microprocessor 12 to achieve the desired pulsatile flow rate of carbon dioxide. To do this the following input data is provided to microprocessor 12. The operator makes a clinical determination of the desired flow rate to be delivered during systole and inputs this into microprocessor 12. The flow rate of carbon dioxide during diastole is a predetermined percentage of the systolic flow rate and in the preferred embodiment of this invention is about twenty percent of the systolic flow rate. An operator inputs into microprocessor 12 a clinically determined volume of carbon dioxide that is to be injected during the injection procedure and also provides the microprocessor with the length and the diameter of catheter 34. Information concerning the patient's cardiac cycle and blood pressure is provided to the microprocessor using conventional means. In the preferred embodiment of the invention blood pressure information is provided by a disposable blood pressure transducer mounted in sterile tube set 15 and cardiac cycle information is provided by coupling injector 10 to a standard 3-lead electrocardiogram. From this input data the microprocessor determines, based on known calibration algorithms, the amplitude and duration of the opening of the valve 20 orifice. The microprocessor 12 synchronizes the opening and closing of the valve 20 orifice to the systolic and diastolic portions of the patient's cardiac cycle so that the flow of carbon dioxide is in turn synchronized to the patient's blood pressure wave.

Figure 2:
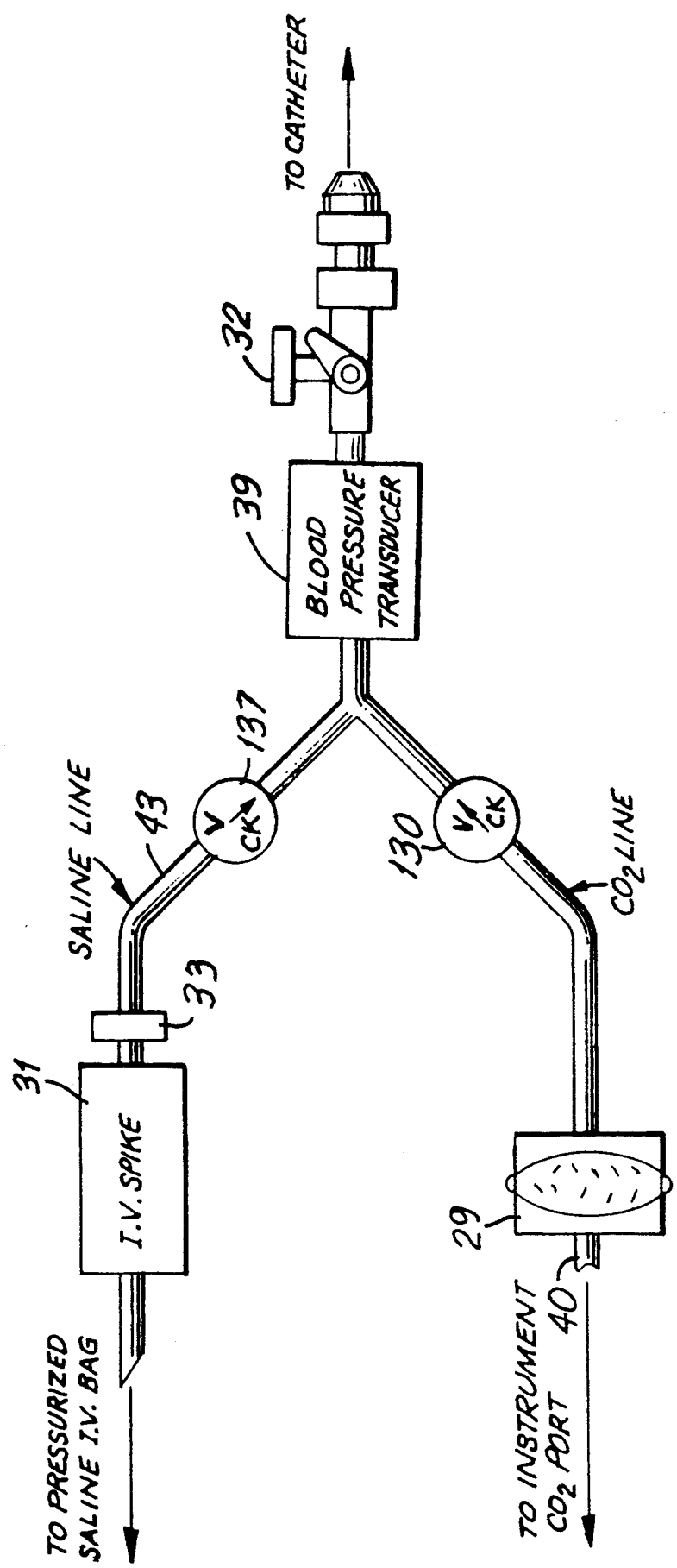
FIG. 2 is a schematic view of one embodiment of the apparatus of the present invention.
Figure 3:
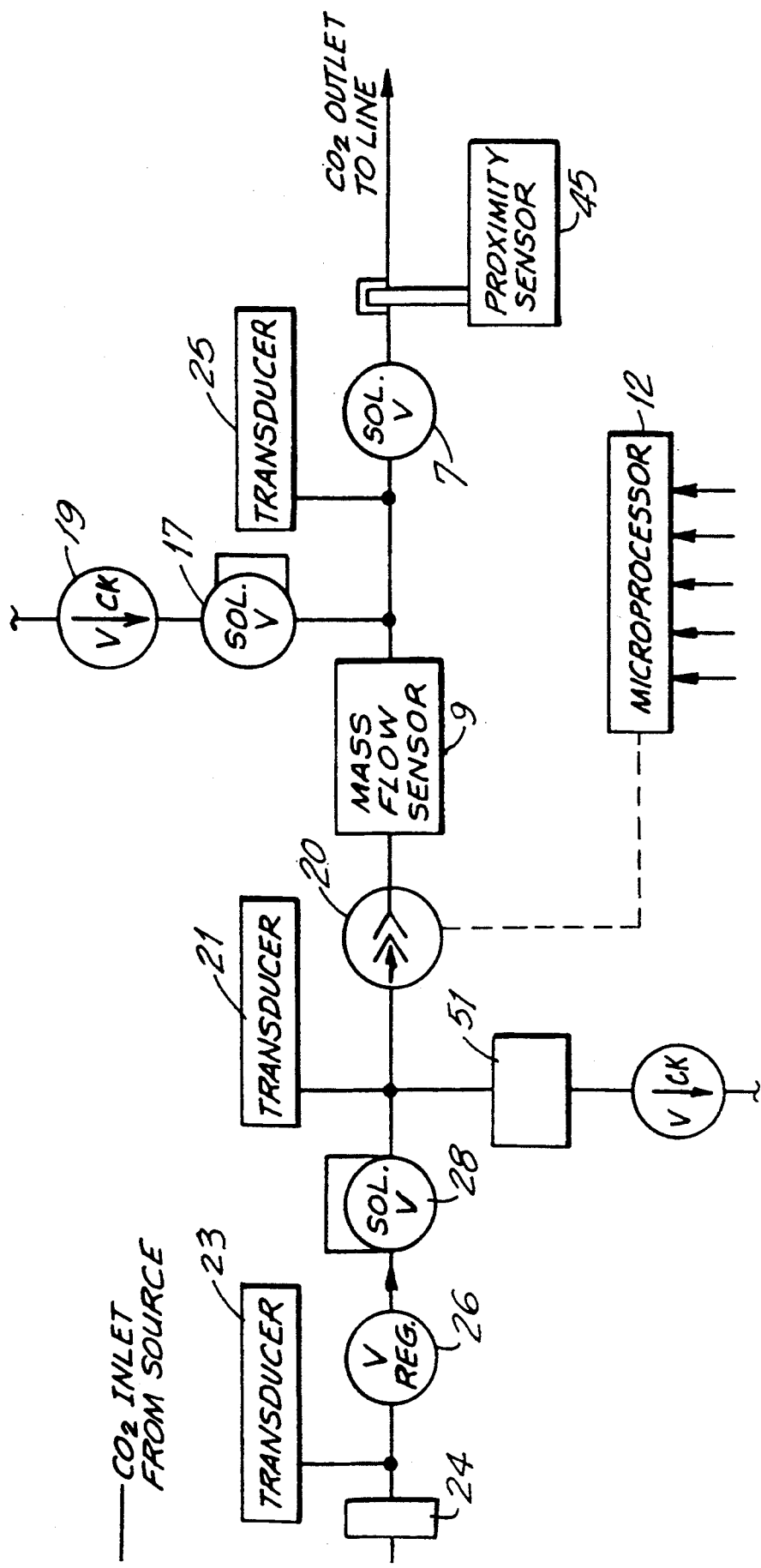
FIG. 3 is a schematic view of a portion of the contrast media injector indicating the path of flow of carbon dioxide therethrough.
Figure 4:
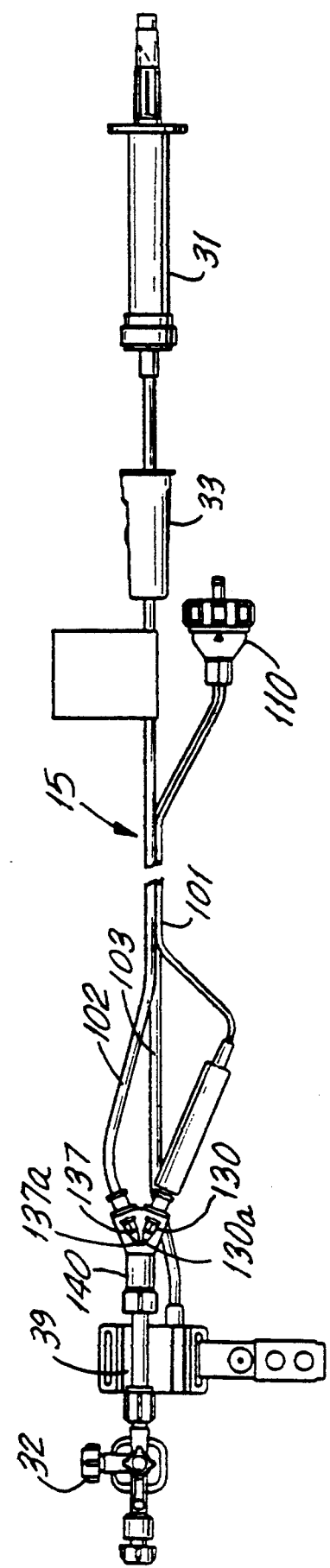
FIG. 4 is a schematic view of one embodiment of the apparatus of the present invention.
Figure 5:
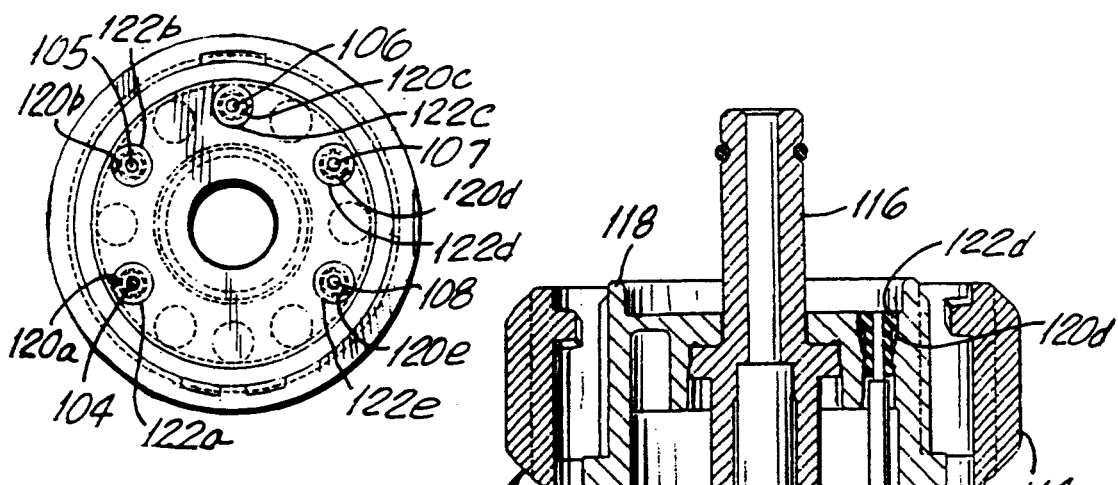
FIG. 5 is a sectional view taken generally along line 5—5 of the FIG. 4 and showing the electro-gas fitting of the apparatus.
Figure 6:
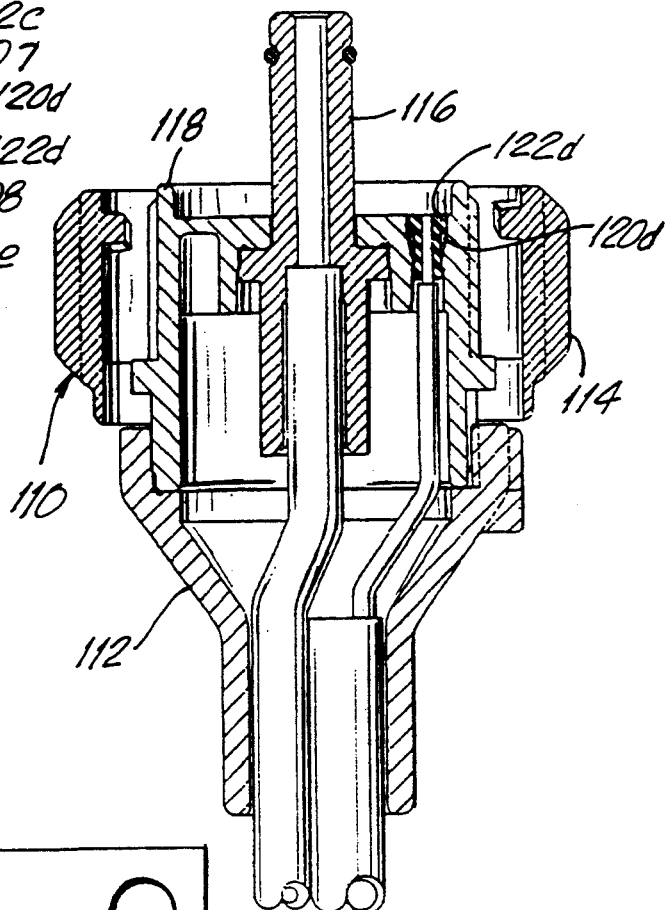
FIG. 6 is a sectional view taken generally along line 6—6 of FIG. 5.
Figure 7:
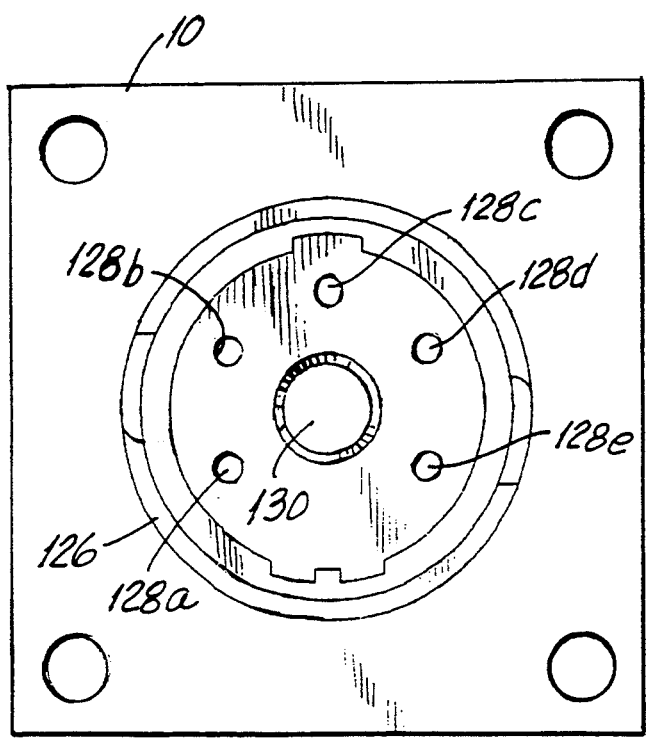
FIG. 7 is a sectional view showing the injector receptacle into which the FIG. 5 fitting connects.
Figure 8:
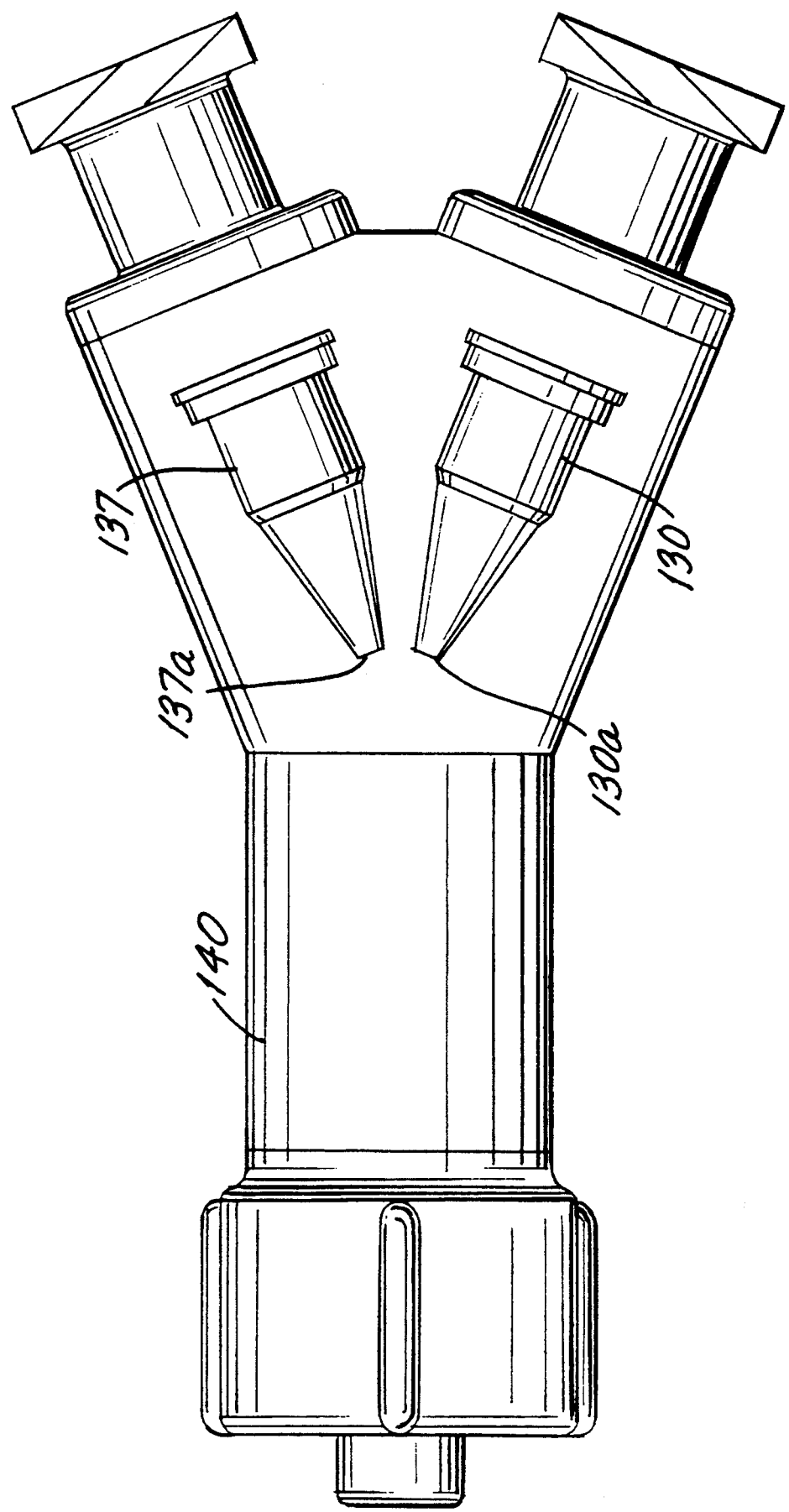
FIG. 8 is an enlarged view of the duckbill valves of the present invention.

Sterile tube set 15, which is disposable, is attached to injector 10. Carbon dioxide and saline are introduced into the patient after passing through sterile tube set 15. In one embodiment of the invention, the sterile tube set 15 includes a sterilizing filter 29. Filter 29, in the preferred embodiment is a 0.2 micron filter to facilitate removal of bacteria and thus keep the carbon dioxide sterile. As shown in FIG. 4, in one embodiment of the invention, sterile tube set 15 includes a bonded tri-lumen tube formed of a first lumen 101 through which the carbon dioxide flows, a second lumen 102 through which the saline flows and third lumen 110 which carries four transducer wires 104, 105, 106, 107 and a ground wire 108. In lieu of a tri-lumen tube, as shown in FIG. 2, conventional separate gas and saline tubes 40, 43 may be used.

When the tri-lumen embodiment is used, all of the wires 104–108, are shielded to protect them from outside interference. In this embodiment, gas lumen 101 and wire lumen 103 are connected to an electro-gas fitting 110. Fitting 110 is designed such that gas and electric connections to the injector are made by one fitting. Fitting 110 is designed for relatively inexpensive manufacture and such that it will not adversely effect the fitting receptacle on injector 10. Fitting 110 includes a strain relief cap 112, a rotating collar 114, an O-ring tip 116, a body 118, an O-ring 122, and five wire locks 120a–120e. It is desired to have a flat connecting surface on fitting 110, this is achieved through said wire locks or this may be achieved by using a conductive epoxy in lieu of the wire locks.

Fitting 110 is assembled by ultra-sonically welding O-ring tip 116 into body 118. Wires 104–108 are bonded into the wire locks 120a–120e and the wire locks are press fit into channels 122a–122e of body 118. Wires 104–108 supply a positive supply voltage, a negative supply voltage, a positive signal response, a negative signal response, and a ground.

Gas lumen 103 is bonded to the inner diameter of O-ring tip 16. This allows a path for fluid flow. The distal end of O-ring tip 116 seals onto the injector 10.

Fitting 110 is plugged into a mating receptacle 126 on injector 10. Mating receptacle 126 has five spring loaded pins 128a–128e and a central bore 130. The O-ring tip 116 of fitting 110 is placed in bore 130. The O-ring seals the gas path of the bore 130 before electrical contact is made. This insures that an air tight seal is made before an injection is allowed to be made into the patient. In order for injector 10 to inject into a patient a blood pressure reading must be detected. Having the gas path seal before the electrical contact is made insures a closed system. Once plugged in threads on the collar 114 of fitting 110 and threads of the mating receptacle 126 are tightened by turning the collar a one-quarter to one-half turn. The fitting body 118 is keyed to insure proper alignment of the wire locks on the fitting to the pins on the mating receptacle.

The use of spring loaded pins on the injector receptacle increases the life of said receptacle from approximately 5,000 cycles to 50,000 cycles. By designing fitting 110 with a flat conductive surface it is possible to use these spring loaded pins in place of a more conventional socket design. Conventional sockets will eventually wear out, as stated, after approximately 5,000 pin insertions. To replace them is either a costly field service trip or an inconvenient return of the product to the factory for repair.

In the preferred embodiment of the invention sterile tube set 15 includes two duckbill check valves 130, 137. The valves 130, 137 are designed such that near total evacuation of carbon dioxide or saline may be accomplished. The duckbill valves open at a pressure of about 0.34 psi and close at a back pressure of about 0.34 psi. The near total evacuation is accomplished by placing the duckbill valves at an angle of between 30° to 45° with their tips 137a, 130a, almost touching and by forming tube 140, downstream of the valves with an inner diameter of between 0.062–0.110 inches. This design minimizes dead space downstream of the valves and insures a solid column of saline during blood pressure readings which is needed to avoid dampening of the pressure wave. It also insures a continuous column of carbon dioxide when injecting carbon dioxide. This is important since otherwise droplets of saline can break off and be entrained in the gas flow which could cause erratic delivery of carbon dioxide gas. The valves, in conjunction with a pinch valve (not shown) gate the flow of saline and carbon dioxide such that only one or the other, but not both, can flow downstream of the valves. This is effectuated as follows. Saline continuously flows from a saline source downstream towards the valves at a pressure of over 0.34 psi to thus open valve 137. When carbon dioxide is injected an external pinch valve (not shown) occludes the saline tube and stops saline flow. Check valve 137 closes when the back pressure of CO2 flow is applied to the check valve 137. This further isolates the saline from CO2. Since the pinch valve has stopped saline flow, the minimum pressure of CO2 needed to close the valve 137 is 18mmhg. This valve serves two purposes by isolating saline from CO2. One, back pressure of CO2 will not cause CO2 to flow into the saline tube. If CO2 were to do this, the delivery amounts of CO2 into the patient could be affected as far as accuracy. Also, there is a reduced possibility of trapping a gas bubble which could cause erroneous blood pressure readings. Secondly, it eliminates the possibility of entraining saline into the CO2 flow.

When carbon dioxide is not being injected into a patient, through tube set 15, a saline drip is flowing through tube set 15 to prevent clotting of blood in the catheter. The carbon dioxide flows through tube set 15 after it has gone through injector 10. Sterile tube set 15 thus couples both a saline source and injector 10 to catheter 34.

The path of flow of saline is as follows. Pressurized saline from a bag 22 or other source is connected to sterile tube set 15 using spike 31. A roller clamp 33 and an external pinch valve 35 are provided to control the flow of saline. The saline flows through check valve 137 which prevents reflux of carbon dioxide into the saline bag 22. The saline then flows through blood pressure transducer 39 and then through a high pressure three-way stopcock 32 into catheter 34. External pinch valve (not shown) is an additional back-up measure used to insure that saline and carbon dioxide do not simultaneously flow into the catheter especially at very low pressure carbon dioxide flow, and also to insure that saline flows into the catheter whenever carbon dioxide does not so flow.

The path of flow of the carbon dioxide is as follows. After leaving its source the carbon dioxide flows into injector 10. In injector 10 the carbon dioxide flows past a two micron filter 24 which removes gross particulate contaminate from the carbon dioxide. It next flows through a pressure regulator 26 which lowers the pressure as fed from the source and standardizes the pressure of the carbon dioxide in the injector. After that the carbon dioxide flows through an on/off valve 28 which is capable of halting the flow of the carbon dioxide in injector 10. The carbon dioxide then flows through valve 20. After flowing through valve 20, the carbon dioxide flows through a mass flow sensor 9 which feeds instantaneous flow rate data to microprocessor 12. The carbon dioxide then flows through on/off valve 7 immediately proximal to the point of connection of the tube set 15 to injector 10. Then the carbon dioxide exits injector 10 and flows into tube set 15 where it flows through sterilizing filter 29, a check valve 130, blood pressure transducer 39 and stopcock 32 into the patient via catheter 34. All of the valves and filters in the sterile segment 15 are hermetically sealed and bonded.

In use, catheter 34 is introduced into a patient, and then the sterile segment 15 is connected to the catheter. The stopcock 32 is put in a back flow position to evacuate air from the catheter 34.

Prior to commencing an injection of carbon dioxide and after the connection of the catheter to the tube set 15, injector 10 is purged. The purge removes ambient air, which contains a high percentage of nitrogen, from the apparatus to insure patient safety. During this purge the carbon dioxide is allowed to run through injector 10 and tube set 15 with stopcock 32 in its open position to vent the air in the system to the atmosphere. After a sufficient volume of carbon dioxide is run through the injector, the stopcock 32 is placed in its injecting position. A purge cycle must be run anytime the tube set 15 has been disconnected from the injector 10 and anytime a new source of carbon dioxide is connected to injector 10.

At the beginning of each injection a predetermined volume of carbon dioxide is dispensed into tube set 15. The volume of carbon dioxide dispensed is just enough to clear the saline from the tube set 15 and catheter 34. The purpose of this is to establish a continuous column of carbon dioxide between the source and the patient. Because of its gaseous nature the carbon dioxide compresses when exposed to pressure. This presents a problem when an injection commences. Without this flushing injection of carbon dioxide, the gas would compress further as it pushed the column of saline. This compression would be relieved in the form of a transient explosion as the carbon dioxide reached the end of the catheter. To prevent this, a continuous column of carbon dioxide between injector 10, the tube set 15 and the patient's blood stream is created prior to injection. This continuous column of carbon dioxide is generated by flushing out the saline in the system using the small volume injection of carbon dioxide to push the saline out in front of it. Too much carbon dioxide, at this point, would cause explosive decompression and blood vessel damage.

As soon as adequate time has elapsed to allow the predetermined volume of carbon dioxide to expand through the tube set 15 and the catheter, injection at the predetermined systolic and diastolic flow rate is commenced. Injection commences upon the detection of an R-wave peak. And, as heretofore set forth, the orifice of valve 20, under the control of microprocessor 12, will open and close synchronous to the systolic and diastolic portions of the patient's cardiac cycle to thus vary the pulse flow rate of the carbon dioxide into the patient so as to enable total displacement of blood in the area of interest. The systolic segment time and diastolic segment time are determined by the blood pressure transducer 39 using known relationships. Injection will proceed until the amount of carbon dioxide previously determined by the operator has been delivered. This injection will generally extend through a plurality of cardiac cycles.

At the completion of an injection, residual compressed carbon dioxide is vented to the atmosphere through a solenoid valve 17. The venting of this residual gas prevents additional carbon dioxide from being accidentally injected into the patient. Valve 17 remains open until a pressure transducer 25 senses that the residual pressure in the injector is nominally above physiologic pressure.

Injector 10 includes a number of mechanisms for enhancing the safety of the injection procedure. Additional safety is provided by pressure transducer 23 which measures the pressure in the carbon dioxide source. This pressure information is used to determine if the source contains an adequate amount of carbon dioxide for the injection and to determine if the source is connected to the injector 10. If there is not sufficient carbon dioxide for an injection, the microprocessor will not allow an injection to commence. If the carbon dioxide source has been disconnected, the microprocessor will give an appropriate signal to alert the operator that a purge of the system must be run prior to an injection.

For additional safety, mass flow sensor 9 is used to determine instantaneous flow rate through injector 10 and to determine the total amount of carbon dioxide delivered during an injection. If the instantaneous flow rate is not within input parameters or if the predetermined volume has been delivered microprocessor 12 will halt the injection. An additional safety mechanism is provided by having microprocessor 12 calculate the expected duration of an injection and having the microprocessor time the actual injection. Again, microprocessor 12 will terminate injection where the desired volume has not been delivered in the expected time.

Signals from pressure transducer 21 are also used to monitor the functioning of pressure regulator 26 and to give an appropriate message if the pressure regulator 26 is not working correctly.

A gas sensor 51 may be placed in injector 10 to sample the carbon dioxide for possible contamination. In a preferred embodiment, gas sensor 51 is a fast acting oxygen sensor with sensitivity in the ppm range. The exhausted gas from sensor 51 is vented to atmosphere through a one-way check valve to ensure no entrainment of room air into the carbon dioxide gas stream.

Proximity sensor 45 is used to detect if sterile segment 15 is connected to injector 10. This information is used by microprocessor 12 to determine if a purge cycle needs to be run.

Panel 47 is used to input data into microprocessor 12 and is further used to display information to the operator.

Catheter 34 is disposable and catheters of different lengths and diameter are contemplated for use in apparatus 10, the length and diameter of the catheter being selected by the operator based upon varied criteria including the vessel into which the carbon dioxide will be injected.

As stated heretofore tube set 15 is disposable and it is contemplated that a new sterile segment will be used for each patient.

Injector 10 provides a safe and efficient way to deliver a pulsatile flow of carbon dioxide to a patient to enable the carbon dioxide to serve as a contrast media.

Blood Pressure Transducer 39 is monitored to ensure that the tube set 15 is not connected to a patient prior to allowing a purge to commence. This monitoring is done by determining if a blood pressure wave form can be detected. The detection of such a wave form indicates that stopcock 32 is not in the correct position for the purge sequence. The energy needed to power blood transducer 39 is conducted from the injector through wires 104–108.

For safety the pressure in the carbon dioxide source should be constant. This pressure is monitored using transducer 23. If there is a drop in this pressure after a purge cycle, another purge cycle is required prior to commencing an injection.

The actual flow rate delivered by injector 10 is a function of gas pressure on the upstream side of valve 20, control current provided to valve 20 and the size and length of the catheter 34. To insure flow rate accuracy the upstream gas pressure should be at a stable pre-set value and this pressure is monitored using pressure transducer 21.

R-wave internal is measured by microprocessor 12 to ensure that it is within physiologically normal ranges. Additionally, R-wave interval is monitored during an injection to ensure that there is continuity of R-waves during the injection. The purpose of these monitoring functions is to ensure that clinically efficacious studies are generated from each injection and that the patient is not exposed to more carbon dioxide than necessary.

Microprocessor 12 is programmed to limit injection volume to 1000 cc to prevent excessive injection volumes from being administered which could result in carbon dioxide build-up resulting is ischemia.

What is claimed is:

1. An apparatus for use with a contrast media injector of the type including a source of gas and a source of liquid, the apparatus comprising:
   a gas delivery channel;
   means for connecting said gas delivery channel to a gas source;
   a liquid delivery channel;
   means for connecting said liquid delivery channel to a liquid source;
   electro-conductive wires connectable to a power source;
   a plurality of normally closed, automatic valves for controlling the flow of gas and liquid from said gas and liquid channels, said normally closed valves including means for opening in response to predetermined internal pressures, a said normally closed valves including means for insuring that the gas and liquid do not simultaneously exit from said gas and liquid channels, when the back pressure of the gas is greater than the back pressure of the liquid, said normally closed valves minimizing inadvertent mixing of said gas and liquid;

said means for connecting said gas channel to said gas source including means to connect said electro-conductive wires to a power source.

2. The apparatus of claim 1 wherein said plurality of normally closed valves includes two duckbill check valves placed at an angle of between 30° to 45°, and further included a common channel through which either gas or liquid flows after exiting said duckbill valves, said common channel having an inner diameter of between 0.062 to 0.110 inches.

3. The apparatus of claim 1 and further comprising a channel in which said electro-conductive wires are housed.

4. The apparatus of claim 1 wherein said gas delivery channel, said liquid delivery channel and, said channel housing said electro-conductive wires are three lumens of a bonded tri-lumen tube.

5. The apparatus of claim 1 and further including a receptacle on said contrast media injector, and wherein said means for connecting said gas channel and said electro-conductive wires to a gas source and a power source is a fitting, said fitting including wire locks, said wire locks constructed to mate with spring loaded pins on said receptacle.

6. The apparatus of claim 5 wherein the portion of said fitting which mates with said receptacle is flat.

7. The apparatus of claim 6 wherein said fitting includes wire locks and said receptacle includes spring loaded pins, the wire locks engaging the spring loaded pins.

8. The apparatus of claim 6 wherein said fitting includes a conductive epoxy and said receptacle includes spring loaded pins and the epoxy engaging the spring loaded pins.

9. The apparatus of claim 6 wherein said fitting includes an O-ring and an O-ring tip and wherein said receptacle includes a central bore, the O-ring tip being shaped and dimensioned to fit in said bore, said O-ring sealing said bore before electrical contact is made.

* * * * *